United States Patent
Gunderson et al.

(10) Patent No.: US 8,942,795 B2
(45) Date of Patent: Jan. 27, 2015

(54) IMPLANTABLE MEDICAL DEVICE WITH REAL TIME T-WAVE OVERSENSING DETECTION

(75) Inventors: Bruce D. Gunderson, Plymouth, MN (US); Amisha S. Patel, Maple Grove, MN (US); Chad A. Bounds, Minneapolis, MN (US)

(73) Assignee: Medtronic, Inc., Minneapolis, MN (US)

(*) Notice: Subject to any disclaimer, the term of this patent is extended or adjusted under 35 U.S.C. 154(b) by 2250 days.

(21) Appl. No.: 11/096,851

(22) Filed: Mar. 31, 2005

(65) Prior Publication Data

US 2006/0224075 A1 Oct. 5, 2006

(51) Int. Cl.
*A61B 5/0452* (2006.01)
*A61N 1/362* (2006.01)
*A61B 5/0464* (2006.01)
*A61N 1/37* (2006.01)
*A61N 1/39* (2006.01)

(52) U.S. Cl.
CPC .......... *A61N 1/3621* (2013.01); *A61B 5/04525* (2013.01); *A61B 5/0464* (2013.01); *A61N 1/3702* (2013.01); *A61N 1/3925* (2013.01)
USPC ............................. 600/518; 600/521; 600/516

(58) Field of Classification Search
CPC .. A61B 5/0452; A61B 5/0456; A61B 5/0468; A61B 5/0472
USPC .......................................... 600/518, 516, 521
See application file for complete search history.

(56) References Cited

U.S. PATENT DOCUMENTS

| 5,321,618 | A | 6/1994 | Gessman |
| 5,718,242 | A | 2/1998 | McClure et al. |
| 5,827,196 | A * | 10/1998 | Yeo et al. ...................... 600/509 |
| 6,625,490 | B1 | 9/2003 | McClure et al. |
| 2003/0204215 | A1 | 10/2003 | Gunderson et al. ............. 607/27 |
| 2004/0015197 | A1* | 1/2004 | Gunderson ...................... 607/27 |
| 2006/0116595 | A1* | 6/2006 | Palreddy et al. ............... 600/516 |

FOREIGN PATENT DOCUMENTS

| WO | WO 2004/103172 A2 | 2/2004 | ............... A61B 5/00 |
| WO | WO2004093974 | 11/2004 | |

* cited by examiner

*Primary Examiner* — Joseph Stoklosa
(74) *Attorney, Agent, or Firm* — Michael J. Ostrom; Stephen W. Bauer

(57) ABSTRACT

An implantable cardioverter defibrillator (ICD) senses ventricular depolarizations (R-waves) in an electrogram signal to detect a ventricular tachycardia or fibrillation episodes. The EGM signal is also monitored in real time for characteristics that uniquely identify instances of T-wave oversensing. The ICD determines whether detection of a tachycardia or fibrillation episode is appropriate based upon counts of each of the unique characteristics evidencing T-wave oversensing.

21 Claims, 4 Drawing Sheets

IMPLANTABLE MEDICAL DEVICE WITH REAL TIME T-WAVE OVERSENSING DETECTION

FIELD OF THE INVENTION

The present invention relates to an implantable medical device (IMD), and more particularly, to an implantable medical device that automatically identifies T-wave oversensing on a real-time basis.

BACKGROUND OF THE INVENTION

An implantable cardioverter defibrillator (ICD) is an IMD that is capable of detecting a tachyarrhythmia (i.e. a fibrillation or abnormal high rate tachycardia) in a heart chamber and providing a high energy electrical shock into or across cardiac tissue to terminate the detected tachyarrhythmia. The ICD typically uses leads inserted into or positioned adjacent the heart chamber to sense electrical activity in the chamber. Cardiac depolarizations are sensed by sense amplifiers having inputs coupled to electrodes carried by the leads. The intervals between sensed depolarizations are measured and compared to threshold intervals to determine whether the chamber is in normal sinus rhythm, tachycardia, or fibrillation.

When detection criteria are met indicating tachycardia, the ICD may first attempt to terminate the tachycardia through anti-tachycardia pacing (ATP), which uses low energy pacing pulses. If ATP therapy is unsuccessful, then a high energy cardioversion shock, synchronized to sensed depolarization, is attempted. If fibrillation is detected, a high energy shock may be delivered without synchronization, and is referred to as a defibrillation shock.

To monitor ventricular tachyarrhythmia, the ICD senses ventricular depolarizations or -R-waves-. For accurate tachyarrhythmia detection, only one event (the R-wave) should be sensed during each normal sinus cardiac cycle. Oversensing of events other than the R-wave can result from sensing cardiac events such as ventricular repolarizations (T-waves) and far field R-waves, from double counting R-waves, and from sensing non-cardiac signals such as myopotentials from surrounding muscle tissue, noise from electromagnetic interference (EMI) external to the patient, or noise produced by a lead failure due to failed insulation, broken conductors or a poor connection to the ICD.

T-wave oversensing results when two ventricular sensed events occur during a cardiac cycle, one coinciding with the R-wave (depolarization) and the other coinciding with the T-wave (repolarization). T-wave oversensing can occur when there is a reduction in the R-wave amplitude (for example, due to a microdislodgement of the lead) or as a result of an increased T-wave amplitude (for example, due to a chemical/drug imbalance).

Oversensing T-waves by the ICD sense amplifiers can result in inappropriate shock therapies, which are painful to the patient and which waste energy and shorten the operating life of the ICD. In addition, timing either ATP or cardioversion to a T-wave that is incorrectly identified as an R-wave may induce an arrhythmia when one did not in fact exist.

BRIEF SUMMARY OF THE INVENTION

The present invention addresses the problem of T-wave oversensing in an ICD by incorporating into the determination of tachyarrhythmia an evaluation of characteristics that indicate T-wave oversensing. The evaluation of the T-wave oversensing characteristics is done on a event-by-event basis, so that corrections for T-wave oversensing are made on a real-time continuous basis.

BRIEF DESCRIPTION OF THE DRAWINGS

These and other advantages and features of the present invention will be appreciated as the same becomes better understood by reference to the following detailed description of the preferred embodiment of the invention when considered in connection with the accompanying drawings, in which like numbered reference numbers designate like parts throughout the figures thereof, and wherein.

DETAILED DESCRIPTION OF THE INVENTION

Figure 1:
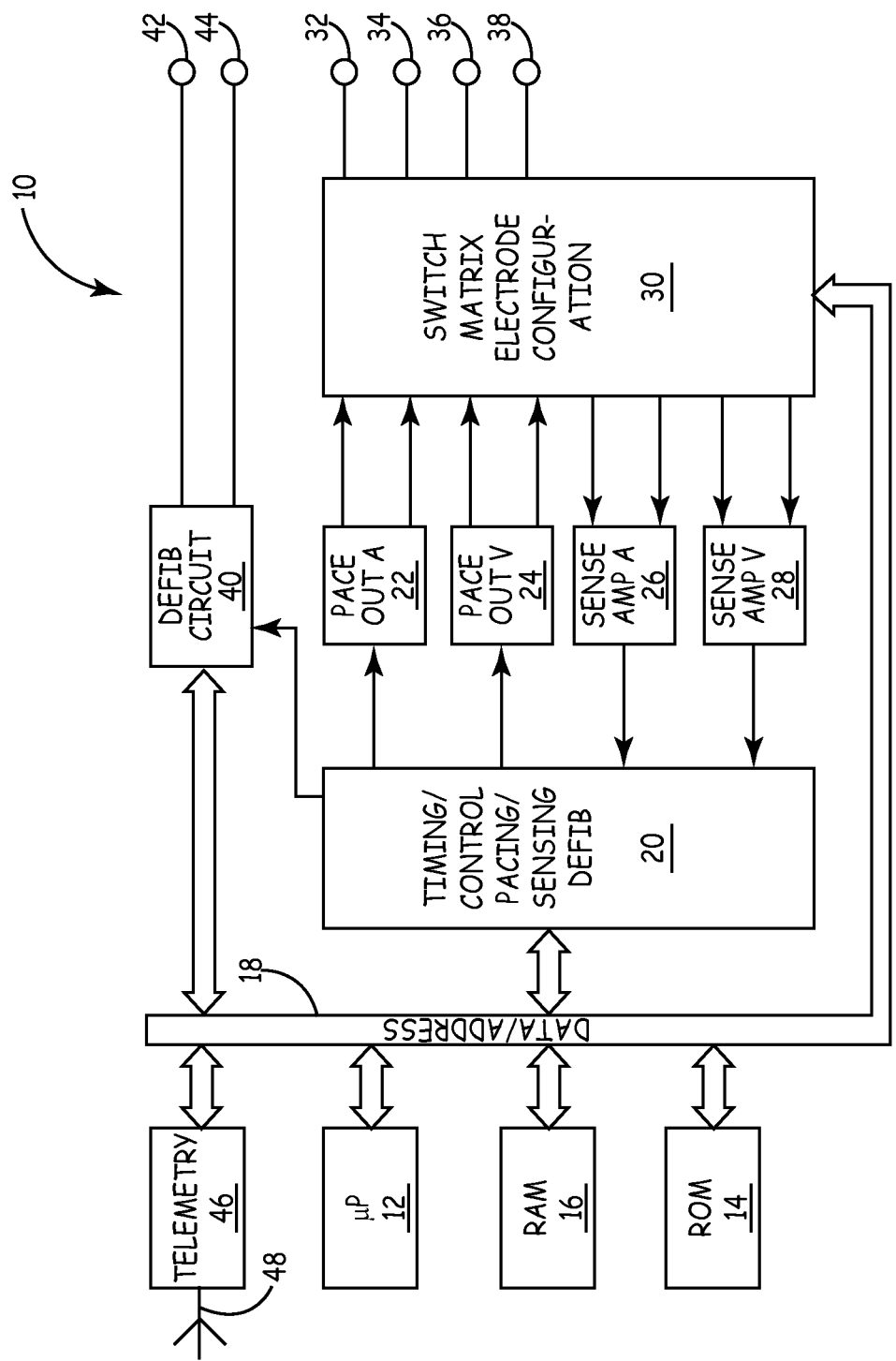
FIG. 1 is a block diagram of an implantable cardioverter defibrillator configured to employ the real-time T-wave oversensing feature of the present invention.

FIG. 1 is a block diagram of implantable cardioverter defibrillator (ICD) 10 that is configured to provide pacing and cardioversion/defibrillation therapy to the atria and ventricles of a patient's heart. ICD 10 senses electrical activity of the heart, and determines whether the atria and the ventricles are in normal sinus rhythm, or whether tachycardia or fibrillation of either the atria or the ventricles is occurring. Based upon the sensed electrical activity and stored programmed instructions, ICD 10 may provide anti-tachycardia pacing (ATP) therapy, cardioversion shocks, or defibrillation shocks.

ICD 10 includes microprocessor 12, read only memory (ROM) 14, random access memory (RAM) 16, data/address bus 18, timing/control circuitry 20, atrial pacing output circuit 22, ventricular pacing output circuit 24, atrial sense amplifier 26, ventricular sense amplifier 28, switch matrix 30, atrial pace/sense electrodes 32 and 34, ventricular pace/sense electrodes 36 and 38, defibrillation circuit 40, atrial defibrillation electrode 42, ventricular defibrillation electrode 44, telemetry circuit 46, and antenna 48.

Microprocessor 12 controls ICD 10 based upon programmed instructions read from ROM 14 or RAM 16. Programmed instructions include parameters for various modes of therapy that can be provided, algorithms for analyzing sensed cardiac events and electrogram (EGM) waveforms in order to detect whether the heart is in a normal sinus rhythm or is in an episode of tachycardia or fibrillation, and algorithms for selecting the appropriate therapy. With the present invention, microprocessor 12, based on instructions stored in ROM 14, performs a real-time monitoring of three characteristics indicative of T-wave oversensing, and withholds a detection of ventricular tachycardia (VT) or ventricular fibrillation (VF) when those characteristics indicate T-wave oversensing has occurred.

RAM 16 is used to store physiological signal data including, for example, EGM waveform data. The data stored in RAM 16 may be used by microprocessor 12 for therapy delivery and diagnostic purposes, and may also be transferred to an external device using telemetry circuit 46 and antenna 48.

Microprocessor 12 is coupled to timing/control circuitry 20 through bus 18. Microprocessor 12 controls timing/control circuitry 20 to deliver pacing pulses at appropriate times, according to a particular mode or therapy selected by microprocessor 12. Based upon control signals from microprocessor 12, timing/control circuitry 20 provides output pulses to output circuits 22 and 24 to provide pacing pulses, and to defibrillation circuit 40 to provide cardioversion or defibrillation shocks. Timing/control circuitry 20 receives inputs from sense amplifiers 26 and 28.

Atrial sense amplifier 26 receives an atrial EGM signal sensed by atrial pace/sense electrodes 32 and 34. It provides an atrial sense signal to timing/control circuitry 20 each time a P-wave, representing an atrial depolarization, is sensed. Sense amplifier circuit 26 can also provide an atrial EGM signal to timing/control circuitry 20 for digitizing and storage in RAM 16.

Ventricular sense amplifier 28 receives a ventricular EGM signal from ventricular pace/sense electrodes 36 and 38. The output of ventricular sense amplifier 28 is a ventricular sense signal indicating detection of an R-wave representing a ventricular depolarization. Ventricular sense amplifier 28 can also provide a ventricular EGM signal to timing/control circuitry 20 for digitizing and storage in RAM 16.

Switch matrix 30 selectively connects atrial pacing output circuit 22 and atrial sense amplifier 26 to atrial pace/sense electrodes 32 and 34. Similarly, switch matrix 30 selectively connects ventricular pacing output circuit 24 and ventricular sense amplifier 28 to ventricular pace/sense electrodes 36 and 38.

Defibrillation circuit 40 includes high voltage capacitors and charging circuits necessary to produce the high voltage defibrillation or cardioversion shock through atrial defibrillation electrode 42 or ventricular defibrillation electrode 44. In this example, defibrillation circuit 40 delivers the high voltage shock between one of the electrodes 42 or 44 and the housing or can of ICD 10.

Telemetry circuit 46 and antenna 48 permit two-way communication between ICD 10 and an external device. Data stored in RAM 16 can be transferred out of ICD 10 through telemetry circuit 46 and antenna 48 for use by a clinician, storage in a patient record, or other diagnostic and therapy related purposes. In addition, operating parameters and instructions can be downloaded to ICD 10 through antenna 48 and telemetry circuit 46.

Microprocessor 12 determines the existence of arrhythmia based upon time intervals between sensed cardiac events. In the case of the atria, measurement of the time intervals between P-waves sensed can be analyzed to determine when atrial tachycardia or fibrillation is occurring. In the case of the ventricles, the time intervals between R-waves sensed by sense amplifier 28 are used by microprocessor 12 to determine when a ventricular tachycardia or fibrillation is taking place. Once having detected tachycardia or fibrillation, microprocessor 12 selects a therapy and provides control signals to timing/control circuit 20 to initiate that therapy.

Figure 2:
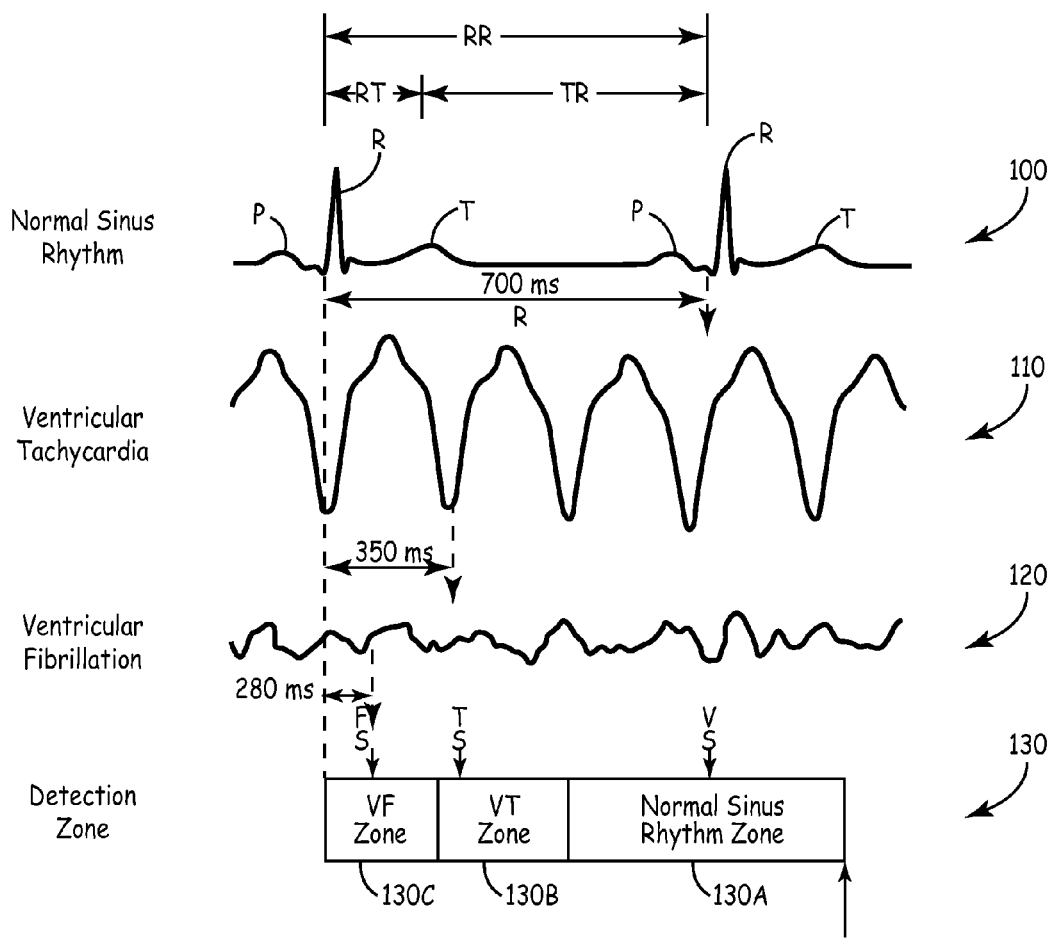
FIG. 2 is a diagram illustrating EGM waveforms representing normal sinus rhythm, ventricular tachycardia (VT) and ventricular fibrillation (VF).

FIG. 2 illustrates how ventricular tachycardia and ventricular fibrillation can be detected based upon information derived from EGM waveforms. Waveform 100 illustrates a normal sinus rhythm, waveform 110 illustrates ventricular tachycardia, and waveform 120 illustrates ventricular fibrillation. Also shown in FIG. 2 is detection zone 130, which shows the time intervals between sensed events that fall within normal sinus rhythm zone 130A, ventricular tachycardia zone 130B, ventricular fibrillation zone 130C, and non-physiological (noise) zone 130D.

Normal sinus rhythm waveform 100 shows two successive heartbeats. Each beat begins with an atrial depolarization, (P-wave) followed by ventricular depolarization (R-wave) and then ventricular repolarization (T-wave). Both the P-wave and the T-wave are typically broader and of lower amplitude than the R-wave.

The wavelength of normal sinus rhythm waveform 100 is measured from the onset of the R-wave to the onset of the next successive R-wave. Ventricular sense amplifier 28 must sense the R-wave, without sensing either the P-wave or the T-wave, and yet be sensitive enough to sense low amplitude ventricular fibrillation. Sense amplifier 28 filters and rectifies the EGM signal and compares the signal to a threshold value. The threshold is set at a percentage of the peak value of the R-wave, and it is then allowed to decay over the interval reading to the next R-wave so that the threshold will be low enough to detect ventricular fibrillation. As long as there is a significant difference in amplitude between the R-wave and the T-wave, the threshold will still be higher than the T-wave at the time that the T-wave occurs. However, if the amplitude of the R-wave is diminished (for example by a partial dislocation of ventricular electrodes 36 or 38) or if the amplitude of the T-wave is increased (such as by a chemical or drug imbalance), sense amplifier 28 may erroneously sense a T-wave as an R-wave. T-wave oversensing events may occur with every beat, or only with some beats.

In the example shown in FIG. 2, waveform 100 has an RR interval of 700 milliseconds, which falls within normal sinus rhythm zone 130A. If, however, the T-wave is erroneously sensed as an R-wave, the RT interval may be short enough to be identified as either falling within VT zone 130B or within VF zone 130C. Depending upon the heart rate, the TR interval may also be identified as falling within the VT zone 130B or VF zone 130C.

FIG. 2 illustrates three characteristics that can be used to identify T-wave oversensing. First, the RT interval is often different in length from the TR interval. Second, the sum of the RT interval and the TR interval equals the RR interval. Third, the R-wave is generally larger in amplitude and narrower in width than the T-wave. A comparison of morphology of alternating R-waves and T-waves reveals an alternating morphology.

EGM waveform 110 illustrates ventricular tachycardia. The interval or wavelength of VT waveform 110 is shorter than normal sinus rhythm. This is a characteristic that is primarily used by ICD 10 to identify ventricular tachycardia. If the interval between events sensed by ventricular sense amplifier 28 falls into VT zone 130B, that sensed event is identified as a tachycardia sense event (TS).

VT waveform 110 shows a generally regular waveform shape, which is different than the shape of the R-wave shown in normal sinus rhythm waveform 110. A comparison of morphology of the ventricular tachycardia waveform pulses to one another shows relatively little variation. A comparison of the VT-waves to a normal R-wave shows a significant difference in morphology.

Ventricular fibrillation (VF) waveform 120 is distinguished by its relatively low amplitude, its short interval or wavelength, and its irregular morphology. If the sensed interval is shorter than the VT zone 130B, but greater than about 140 milliseconds, the event is classified as a fibrillation sense (FS).

Microprocessor 12 detects ventricular tachycardia (VT) or ventricular fibrillation (VF) by counting the number of TS or FS events. Detection occurs when the number of intervals detected (NID) reaches a preset value.

Microprocessor 12 performs an algorithm that searches for three properties of T-wave oversensing: large successive interval differences, a current interval that equals the sum of the two previous intervals, and alternating morphologies. The first two properties are derived from the current interval RR(I) and the two proceeding intervals RR(I-1) and RR (I-2). Current interval RR(I) is truncated (e.g. divided by 10) to act as a threshold. The following calculations are made:

$$RR1\text{diff}=Abs(RR(I\text{-}1)-RR(I)) \text{ (i.e. successive difference)} \quad \text{Eq. 1}$$

$$RR2\text{diff}=Abs(RR(I\text{-}2)-RR(I)) \quad \text{Eq. 2}$$

$$Rr\text{sum}=RR(I\text{-}2)+RR(I\text{-}1) \quad \text{Eq. 3}$$

$$Rr\text{sumdiff}=Abs(Rr\text{sum}-RR(I)) \quad \text{Eq. 4}$$

$$Rr\text{difdiff}=Abs(Abs(RR(I\text{-}2)-RR(I\text{-}1))-RR(I)) \quad \text{Eq. 5}$$

$$\text{Mindiff}=\text{Min}(RR1\text{diff},RR2\text{diff},Rr\text{sumdiff},Rr\text{difdiff}) \quad \text{Eq. 6}$$

$$Rr\text{trun}=\text{truncated}(RR/10) \text{ to lowest 10 ms.} \quad \text{Eq. 7}$$

A large successive difference exists if the absolute value of RR1dif minus Mindiff is greater than or equal to a floor value, which represents the maximum of either Rrtrun or 30 milliseconds.

$$Abs(RR1\text{diff}-\text{Mindiff})>=\max(Rr\text{trun},30) \quad \text{Eq. 8}$$

If a large successive difference is detected based on these calculations, a large successive difference count (Count 1) is incremented. If a large successive difference is not detected, then Count 1 is decremented. Count 1 is maintained between a minimum of 0 and a maximum of 12, with a threshold level of 8. If the threshold level is met, then there is sufficient evidence that alternating length RR intervals exist, which is the first characteristic of T-wave oversensing.

The second characteristic of T-wave oversensing is that the current interval RR(I) is approximately equal to the sum of the two previous intervals RR(I-1) and RR(I-2). Microprocessor 12 uses the values calculated from the current interval and two previous intervals to see whether the absolute value of the difference between the current interval and the sum of the two previous intervals is less than or equal to the truncated value Rrtrun.

$$Rr\text{sumdiff}<=Rr\text{trun} \quad \text{Eq. 9}$$

If the current RR(I) is equal to the sum of the two previous intervals RR(I-1) and RR(I-2), within a tolerance defined by Rrtrun, then Count 2 is incremented. If Count 2 is greater than 1 for the previous twenty four intervals, then its threshold is met.

The third characteristic of T-wave oversensing, alternating morphologies, makes use of wavelet match scores. The portion of the EGM waveform representing a sensed event is reduced to a set of wavelet values, which are then compared by microprocessor 12 to the wavelet values for a template R-wave. If the sensed event is an R-wave, the percentage match with the template should be high (70% or higher). If a T-wave has been misidentified as an R-wave, the wavelet match to the R-wave template will be low (less than 50%) since the T-wave is much broader and lower amplitude than the R-wave. If T-wave oversensing is occurring, the sensed events will represent an R-wave, then a T-wave, then an R-wave, and so on. This will result in a pattern of a high match score for the R-wave, followed by a low match score for the T-wave, and another high match score for the next R-wave. The three successive sensed events, therefore, show an alternating morphology between high-to-low-to-high match. A similar situation occurs when the sensed events are a T-wave, followed by an R-wave, followed by another T-wave. With that sequence of three events, the match scores will be low-to-high-to-low. Once again, an alternating morphology is present. If three consecutive sensed events have alternating scores greater than the threshold (e.g. at least 50 percentage points), then an alternating morphology counter (Count 3) is incremented.

Ventricular tachycardia (VT) typically exhibits match scores which are less than 70%, but which are relatively consistent, since each pulse is of generally the same shape. Thus, a T-wave oversensing pattern, with its alternating morphology, will not be confused with ventricular tachycardia.

Ventricular fibrillation is (VF) characterized by a waveform which has very low match scores. It does not exhibit the alternating morphology found with a T-wave oversensing pattern.

Figure 3:
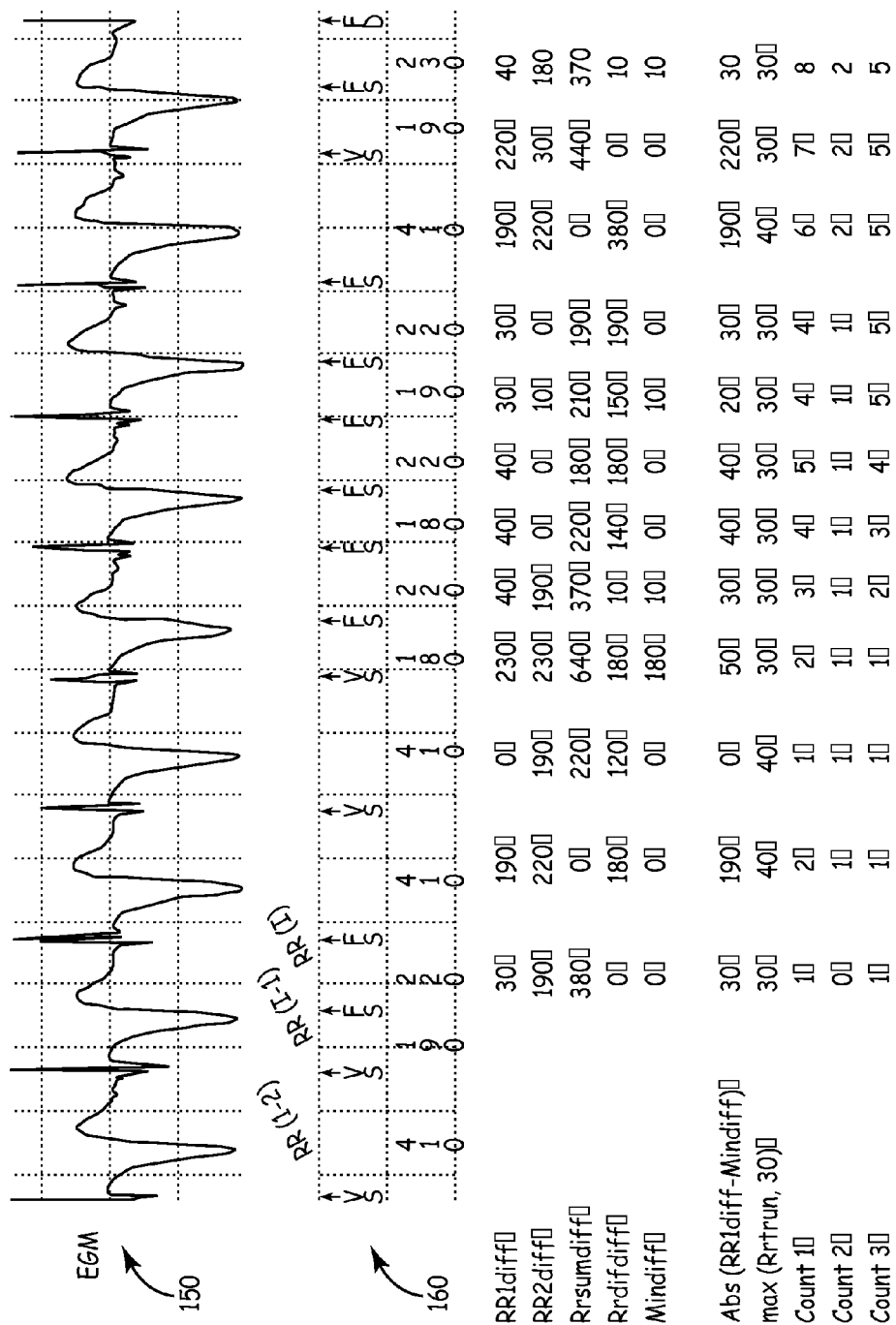
FIG. 3 is a graph showing an example of an EGM waveform in normal sinus rhythm, with sensed events including T-wave oversensing, together with RR interval values, calculations, and running counts used in the real-time T-wave oversensing of the present invention.

FIG. 3 shows an example of a T-wave oversensing pattern and the calculations used to produce Counts 1-3. FIG. 3 includes ventricular EGM waveform 150, marker channel 160, corresponding calculations based on sensed intervals, and Counts 1-3.

Marker channel 160 shows sensed events which are labeled VS, FS and FD in FIG. 3. Those events corresponding to intervals that fall into the normal sinus rhythm range are labeled VS. Events resulting in an interval that falls within the ventricular fibrillation range are labeled FS. With the tenth interval identified as being within the fibrillation range (at the far right end of marker channel 160), a fibrillation detect labeled FD appears. In this example, no sensed interval falls into the VT range, and therefore there are no events labeled TS.

Below the sensed event markers are calculated RR interval values in milliseconds. Thus, the first RR interval is 410 milliseconds. The second interval is 190 milliseconds, the third interval is 220 milliseconds, and so on. By comparing EGM waveform 150 with marker channel 160, a pattern of T-wave oversensing is apparent. Starting from the left end of marker channel 160, the third, seventh, ninth, eleventh, and fourteenth sensed events are T-waves, which result in short intervals that are identified as ventricular fibrillation. In fact, waveform 150 shows a normal sinus rhythm with a generally stable RR interval of approximately 410 milliseconds.

With the real-time T-wave oversensing of the present invention, microprocessor 12 checks Counts 1, 2 and 3 before accepting fibrillation detect event FD as a genuine detection. If Counts 1-3 show evidence that T-wave oversensing contributed to the FD event (as they do in FIG. 3), then detection is withheld. The process repeats itself with each new sensed event.

Figure 4:
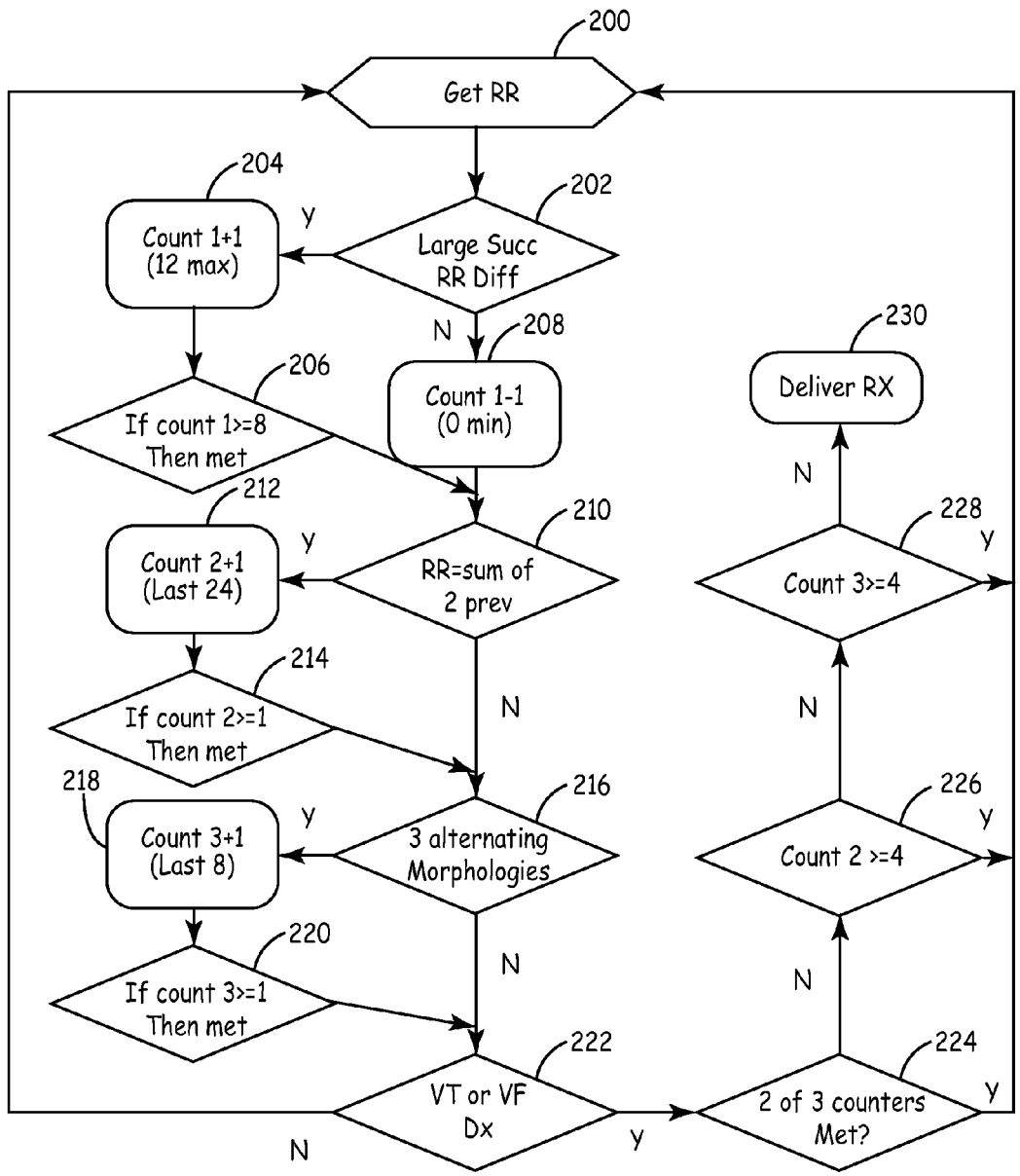
FIG. 4 is a flow diagram showing the use of RR interval patterns and wavelength morphology match scores to detect T-wave oversensing.

FIG. 4 is a flow diagram showing how the present invention is used to identify T-wave oversensing in real time, so that detection of ventricular tachycardia or ventricular fibrillation is withheld if there is evidence of T-wave oversensing. The determination is made on a event-by-event basis as shown in FIG. 4. With each new sensed event, microprocessor 12 gets the RR interval value associated with that sensed event (step 200). Using the calculations which have been described above, microprocessor 12 determines whether a large successive RR difference exists (step 202). If a large successive RR difference exists, Count 1 is incremented up to a maximum value of 12 (step 202). Whenever Count 1 is greater than or equal to 8, microprocessor 12 sets a flag indicating that Count 1 threshold has been met (step 206). If a large successive RR difference is not present with the current interval, Count 1 is decremented toward a minimum value of zero Step 208).

Once Count 1 has been incremented or decremented, microprocessor 12 then determines whether the current interval is equal to the sum of the two previous intervals (step 210). If the answer is yes, Count 2 is incremented (step 212). Count 2 is maintained for only the last 24 intervals, so that Count 2 reflects only recent activity. The threshold for Count 2 is one. If there is one instance in the last 24 intervals where the current interval equals the sum of the two previous intervals, then the Count 2 threshold is met and a flag is set (step 214), and microprocessor 12 moves on to the third category. If the sum of the two previous intervals does not equal the sum of the current interval, microprocessor 12 moves onto the third category. Count 2 is not decremented.

For the third category (alternating morphologies), microprocessor 12 compares the wavelet match score of the current sensed event with the wavelet match scores for the two preceding events (step 216). If a pattern of alternating morphologies exists with those three sensed events (i.e. high-low-high or low-high-low), using the difference between wavelet scores greater than the threshold value (e.g. 50 percentage points), then Count 3 is incremented (step 218). The score in Count 3 is maintained only for the last eight sensed events. If Count 3 is greater than or equal to one, microprocessor 12 sets a flag indicating the Count 3 threshold has been met (step 220). If microprocessor 12 determines that the last three consecutive sensed events do not exhibit alternating morphologies, Count 3 is not changed, it is not decremented.

Microprocessor 12 then checks to see whether either ventricular tachycardia (VT) or ventricular fibrillation (VF) has been detected (Dx) (Step 222). This will occur when the VT or VF NID value is met. If the NID value is not met, microprocessor 12 returns to step 200 and gets the next RR interval.

If the VT or VF NID value has been met, then microprocessor 12 checks the flag to see whether at least two of the three count thresholds have been met (step 224). If the answer is yes, this is evidence of T-wave oversensing. Microprocessor 12 withholds detection and proceeds to step 200 to get the next RR interval. If not, microprocessor 12 then checks to see if there is a large number of instances where the current interval is equal to the sum of the two previous intervals (step 226). This occurs if Count 2 is greater than or equal to 4. If that condition is met, it is strong evidence that the normal sinus rhythm is present. Microprocessor 12 withholds detection and returns to step 200 to get the next RR interval.

If less than two of the count thresholds are met and Count 2 is less than 4, then microprocessor 12 checks for a large alternating morphology count (step 228). This occurs if Count 3 is greater than or equal to 4. If this condition is met, it also is strong evidence that a sinus rhythm is present. Detection is withheld and microprocessor 12 returns to step 200 to get the next RR interval. If not, then detection occurs and therapy (Rx) (if programmed) begins (step 230).

In the example which has been discussed, the interval analysis and the morphology analysis takes place on sensed event-by-event basis. In other embodiments, the wavelet alternating morphology analysis (which is more computation intensive) may not be performed with every sensed event. Instead, the alternating morphology analysis can begin after one or more events have been identified as either a tachycardia sense or a fibrillation sense. For example, a threshold of three tachycardia sense (TS) or fibrillation sense (FS) events may be a threshold for beginning wavelet analysis on an event-by-event basis.

With the present invention, T-wave oversensing is done on a real-time basis, using counts that are being updated on an event-by-event basis. Counts 1, 2 and 3 provide evidence of T-wave oversensing, which is then used whenever the device determines that VT or VF is present. Detection is withheld if the combination of the three counts indicates T-wave oversensing is present, or if one of the counts strongly indicates the presence of T-wave oversensing. Thus, VT or VF detection, and the resulting therapy based on that detection, has been cross-checked for evidence of T-wave oversensing before microprocessor 12 indicates that detection has occurred.

In addition, microprocessor 12 can produce an alert to the detection of T-wave oversensing. When T-wave oversensing is detected, an alert from the ICD 10 can be sounded or sent as a wireless transmission by telemetry circuit 46 and antenna 48 to a wireless receiver. Data received from ICD 10 as part of the alert can be analyzed and presented on a network, such as Carelink, that is accessible by a clinician.

Although the present invention has been described with reference to preferred embodiments, workers skilled in the art will recognize that changes may be made in form and detail without departing from the spirit and scope of the invention.

The invention claimed is:

1. A method of controlling ventricular tachycardia (VT) and ventricular fibrillation (VF) detection in an implantable medical device, the method comprising:
   sensing R-waves in a ventricular electrogram (EGM) signal;
   obtaining time intervals between successive sensed R-waves;
   monitoring a plurality of characteristics indicative of T-wave oversensing;
   wherein monitoring the plurality of characteristics comprises maintaining a first count to track a number of occurrences of large successive interval differences and maintaining a second count to track a number of occurrences of a current time interval being approximately equal to a sum of two preceding time intervals, and
   withholding detection of a VT or VF in response to the first count and second count indicating presence of oversensed T-waves among the sensed R-waves.

2. The method of claim 1 wherein the large differences between successive time intervals are derived from a current time interval and at least one preceding time interval.

3. The method of claim 1, further comprising maintaining a third count to track a number of occurrences of alternating waveform morphologies, wherein withholding detection of a VT or VF in response to the characteristics comprises withholding detection of a VT or VF in response to the third count and one of the first count and second count indicating presence of oversensed T-waves among the sensed R-waves.

4. The method of claim 1 wherein if at least one of the first count and second count does not indicate presence of oversensed T-waves among the sensed R-waves, the method further comprising withholding detection in response to the other one of the first count and the second count reaching a value strongly indicating T-wave oversensing.

5. The method of claim 1, further comprising:
   analyzing a waveform morphology of each sensed R-wave;
   maintaining a third count to track a number of instances of alternating waveform morphologies; and
   withholding detection of the VT or VF if the third count and one of the first count and second count indicate a likelihood of T-wave oversensing.

6. The method of claim 1 wherein maintaining the first count comprises incrementing the first count in response to a large successive difference between the current interval and an immediately preceding interval being present and decrementing the first count in response to a large successive difference not being present between the current interval and an immediately preceding interval.

7. The method of claim 6 wherein maintaining the second count comprises incrementing the second count in response to a current interval being approximately equal to a sum of two preceding intervals, the second count maintained over a predetermined number of intervals.

8. The method of claim 7 wherein monitoring a plurality of characteristics of T-wave oversensing further comprises maintaining a third count to track a number of an alternating waveform morphology, the third count maintained over a second predetermined number of sensed events by incrementing the third count in response to a current sensed R-wave and two immediately preceding R-waves having alternating morphologies.

9. The method of claim 8 further comprising:
comparing the first count to a first count threshold, comparing the second count to a second count threshold, comparing the third count to a third count threshold, and withholding detection of the VT or VF in response to two of the first count, the second count, and the third count exceeding the respective first count threshold, the second count threshold and the third count threshold.

10. The method of claim 9 further comprising:
comparing one of the first count, the second count and the third count to a next threshold in response to the other two of the first count, the second count, and the third count not exceeding the respective first count threshold, the second count threshold and the third count threshold; and
withholding detection of the VT or VF in response to the one of the first count, the second count and the third count exceeding the next threshold.

11. The method of claim 1 wherein maintaining the first count comprises:
determining a first difference between the current interval and the immediately preceding interval;
determining a second difference between the current interval and a next immediately preceding interval;
determining a third difference between the current interval and a sum of the immediately preceding interval and the next immediately preceding interval;
determining a fourth difference between the current interval and a previous successive difference;
determining a minimum of one of the first, second, third and fourth differences; and
adjusting the first count in response to a comparison of the first difference to the minimum.

12. The method of claim 1 wherein the first count and second count are updated with each sensed R-wave.

13. The method of claim 3, further comprising:
comparing at least three successive sensed events to a template R-wave;
classifying each of the three successive sensed events as either a high percentage match or low percentage match based on the comparison;
detecting an occurrence of alternating waveform morphologies when the classification of the three successive sensed events are high-low-high or low-high-low; and
incrementing the third count upon detecting the occurrence of alternating waveform morphologies.

14. An implantable medical device comprising:
at least one sensing electrode to sense an EGM signal from a heart of a patient;
a sense circuit for sensing events representing R-waves in the EGM signal; and
a processor to identify T-wave oversensing by the implantable medical device based on counts of T-wave oversensing characteristics, the processor obtaining time intervals between successive sensed events, maintaining a first count of T-wave oversensing characteristics to track a number of occurrences of large successive interval differences, maintaining a second count of T-wave oversensing characteristics to track a number of occurrences of a current time interval being approximately equal to a sum of two preceding time intervals, and withholding detection of a ventricular tachycardia (VT) or ventricular fibrillation (VF) in response to the first count and the second count indicating presence of oversensed T-waves among the sensed R-waves.

15. The implantable medical device of claim 14 wherein at least one of the first count and second count does not indicate presence of oversensed T-waves among the sensed R-waves and the processor withholds detection of a ventricular tachycardia or ventricular fibrillation if one characteristic count has reached a value strongly indicating T-wave oversensing.

16. The device of claim 14 wherein maintaining the first count comprises incrementing the first count in response to a large successive difference between the current interval and an immediately preceding interval being present and decrementing the first count in response to a large successive difference not being present between the current interval and an immediately preceding interval.

17. The device of claim 16 wherein maintaining the second count comprises incrementing the second count in response to a current interval being approximately equal to a sum of two preceding intervals, the second count maintained over a predetermined number of intervals.

18. The device of claim 17 wherein monitoring a plurality of characteristics of T-wave oversensing further comprises maintaining a third count to track a number of an alternating waveform morphology, the third count maintained over a predetermined number of sensed events by incrementing the third count in response to a current sensed R-wave and two immediately preceding R-waves having alternating morphologies.

19. The device of claim 18 further comprising:
comparing the first count to a first count threshold, comparing the second count to a second count threshold, comparing the third count to a third count threshold, and withholding detection of the VT or VF in response to two of the first count, the second count, and the third count exceeding the respective first count threshold, the second count threshold and the third count threshold.

20. The device of claim 19 further comprising:
comparing one of the first count, the second count and the third count to a next threshold in response to the other two of the first count, the second count, and the third count not exceeding the respective first count threshold, the second count threshold and the third count threshold; and
withholding detection of the VT or VF in response to the one of the first count, the second count and the third count exceeding the next threshold.

21. The device of claim 14 wherein the first count and second count are updated with each sensed R-wave.

* * * * *